United States Patent [19]

Watts et al.

[11] Patent Number: 5,224,954
[45] Date of Patent: Jul. 6, 1993

[54] COMBINATION SURGICAL TROCAR CANNULA AND RAKE ASSEMBLY

[75] Inventors: James M. Watts, Fort Worth; Michael W. Freitas, Irving, both of Tex.

[73] Assignee: Dexide, Inc.

[21] Appl. No.: 656,950

[22] Filed: Feb. 19, 1991

[51] Int. Cl.$^5$ .............................................. A61B 17/28
[52] U.S. Cl. .................................................. 606/205
[58] Field of Search ............... 606/206, 205, 207, 170, 606/171, 198; 128/751; 604/166, 164, 106

[56] References Cited

U.S. PATENT DOCUMENTS

| | | | |
|---|---|---|---|
| 2,670,519 | 3/1954 | Recklitis | 606/206 X |
| 4,393,872 | 7/1983 | Reznik et al. | 606/206 X |
| 4,655,219 | 4/1987 | Petruzzi | 606/206 |
| 4,994,079 | 2/1991 | Genese et al. | 606/206 |

*Primary Examiner*—Michael H. Thaler
*Attorney, Agent, or Firm*—Jackson & Walker

[57] ABSTRACT

A combination surgical trocar cannula and rake assembly is provided. The rake has radially extending tip elements which protrude out an open end of a trocar housing in response to relative longitudinal telescopic manipulation between the housing and the rake mandrel. Upon telescopic expansion between the mandrel and the housing, the rake elements extend radially outwardly of the housing, and sequential telescopic manipulation between the housing and the mandrel, alone or in combination with rotational movement therebetween enable the rake tip elements to grasp a solid element, such as a portion of a bladder, or the like, for movements during surgery performed through an endoscopic trocar. A fluid passageway is defined between the cannula and the rake mandrel to permit introduction of fluid during surgery while the rake is within the cannula, or, alternatively, to provide a vacuum passageway.

26 Claims, 2 Drawing Sheets

COMBINATION SURGICAL TROCAR CANNULA AND RAKE ASSEMBLY

BACKGROUND OF THE INVENTION (1) Field of the Invention

The invention relates to a combination surgical trocar cannula and rake assembly.

(2) Brief Description of the Prior Art

Surgical endoscopic procedures typically follow three steps. First, a cannula, such as a Veress cannula, is inserted through the abdominal cavity through the abdominal wall and the cavity is inflated with insufflating gas which is passed through the cannula tubular housing. After insufflating, a small incision is made in the skin and a standard trocar spike is thrust into the inflated abdomen through the bore of the trocar tube. The spike is inserted for purposes of puncturing or cutting of the abdominal wall and piercing the fascia and peritoneum inside the cavity. After removal of the spike, the suction/irrigation cannula is reinserted through the trocar housing and into the opening so that fluids may be drained from the body cavity. During many endoscopic surgical procedures, it is necessary to move or hold a solid element during the surgical procedure, such as a side or wall of a gallbladder, a blood vessel, a muscle, or the like.

The present invention provides an apparatus which permits the use of one endoscopic surgical instrument for use in draining fluids from a body cavity while, at the same time, providing in the same instrument a rake assembly which can be hand manipulated to grasp or move such solid elements within the body wall during surgery. Additionally, the present device provides a single means for introduction of fluid into the body wall while at the same time providing a rake for movement or holding of such body concurrently with the introduction of the fluid, or during the draining procedure, which may incorporate a vacuum.

SUMMARY OF THE INVENTION

The present invention provides a combination surgical trocar cannula and rake assembly. The apparatus of the present invention includes an elongate tubular housing which is insertable within a trocar and has an open end for introduction through a body wall, during surgery, together with a second opposite end. A control mandrel is concentrically disposed within the housing and is manipulatable in each of rotational and longitudinal directions relative to said housing. Flexible means are provided for grasping or moving a solid member, such as a blood vessel, muscle, the wall or part of a gallbladder or other body, during surgery, the flexible means being extendable through the trocar housing open end and selectively shiftable in response to relative movement between the tubular housing and the control mandrel between a telescopically retracted, radially contracted position, and a telescopically extended, radially expanded position immediate the open end.

In the preferred embodiment, a fluid passageway is provided intermediate the tubular housing and the control mandrel with the port disposed through the housing for introduction of a fluid or a vacuum therethrough, the passageway extending from the port through the open end.

In the preferred form of the invention, a cruciform configuration is defined around the exterior of the control mandrel and comprises a series of alternating peaks and indentures, the area between the peaks and indentures defining the fluid passageway. A slot is circumscribed on the mandrel for receipt of the flexible means with the slot being circumscribed about 180° around the exterior of the mandrel element.

A seal, such as a circumferentially extending elastomeric o-ring seal member, is carried preferably on the mandrel, and dynamically seals along the interior of the elongated housing.

In the preferred form, the flexible means comprises a u-shaped pin member which is held within the groove on the control mandrel such that the u-shaped pin member is in radially contracted position when the mandrel and the housing are in telescopically contracted position, but the u-shaped pin member flexes axially and radially outwardly of the housing upon telescopic expansion at the open end between the housing and the mandrel members, as a result of manipulation of the mandrel by hand application of a surgeon, nurse or other operator. Thus, the initiation of telescopic movements between the housing and the mandrel enable the u-shaped pin member to selectively expand and contract for grasping, pinching, and movement of members during surgical operations, thus concurrently enabling fluid flow into or out of the area of the surgery.

DESCRIPTION OF THE PREFERRED EMBODIMENTS

Figure 1:
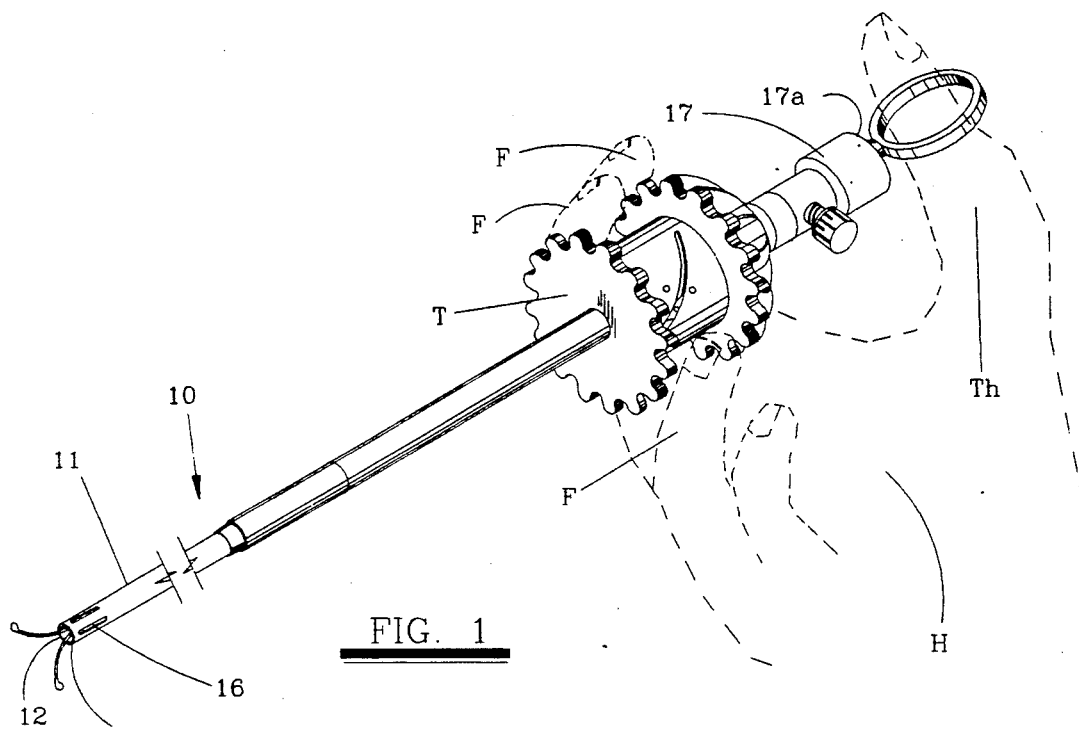
FIG. 1 is an isometric view of the device of the present invention held in the hand of a surgeon.
Figure 3:
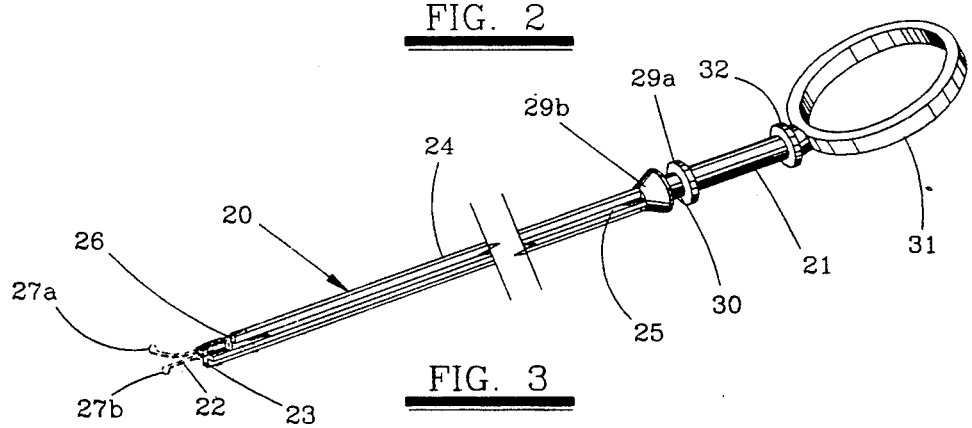
FIG. 3 is an isometric view of the exterior of the rake assembly.

Referring first to FIG. 1, there would be the apparatus of the present invention is held by a hand H of a surgeon, nurse, or other medical operator. The device includes a trocar cannula 10 which includes a trocar tubular housing 11, interiorly of which is disposed a rake assembly 20 (FIG. 3).

As shown in FIG. 1, the trocar T is held in the fingers F with the thumb TH of the hand H disposed through a handle 31 of the rake assembly 20. A cap 17 is secured around the outboard-most end of the tubular housing 11 having a frontal cap top or surface 17a facing the handle 31.

The tubular housing 11 has an open end 12 at its inboard-most end and a second opposite end 13 (FIG. 2) facing the handle 31. The tubular housing 11 has an open end 12 which, during surgery, is disposed through a body wall and into a cavity within which surgery is to be performed. The tubular housing 11 at the open end 12 has a circumferentially extending shoulder 15 for selective interface with first and second tip members 27a, 27b of the flexible means 22 of the rake assembly 20 (FIG. 3).

Immediate the open end 12 of the tubular housing 11 is a series of radially extending rectangularly shaped transverse fluid openings 16 which permit fluid to pass thereacross, either into the cavity from the interior of the tubular housing 11, or from the cavity to the tubular housing 11, as described below.

Figure 2:
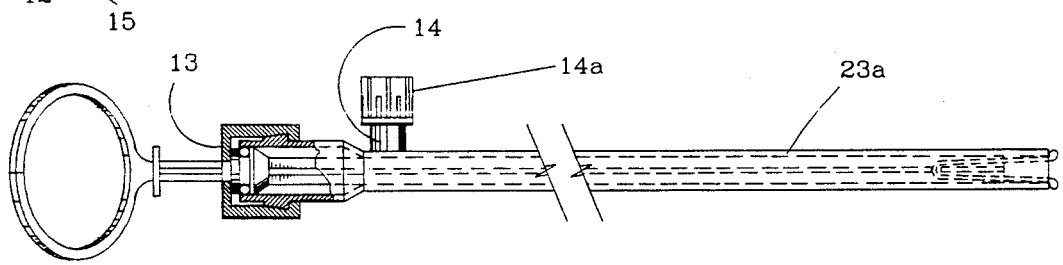
FIG. 2 is a longitudinal sectional illustration of the trocar tubular housing with the rake assembly disposed therein.
Figure 4:
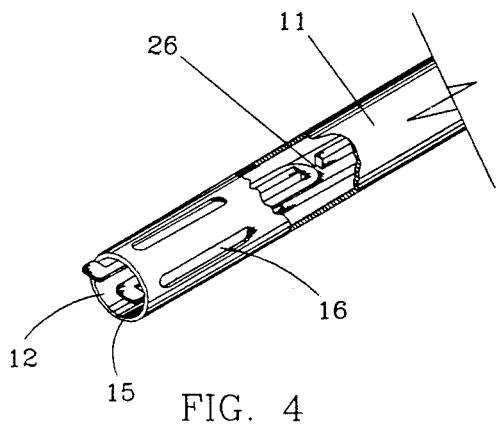
FIG. 4 is an enlarged isometric partial view of the outermost end of the rake assembly, illustrating the open end of the tubular housing and the interrelationship of the flexible means thereto when the housing and the mandrel are in telescopically retracted position.
Figure 5:
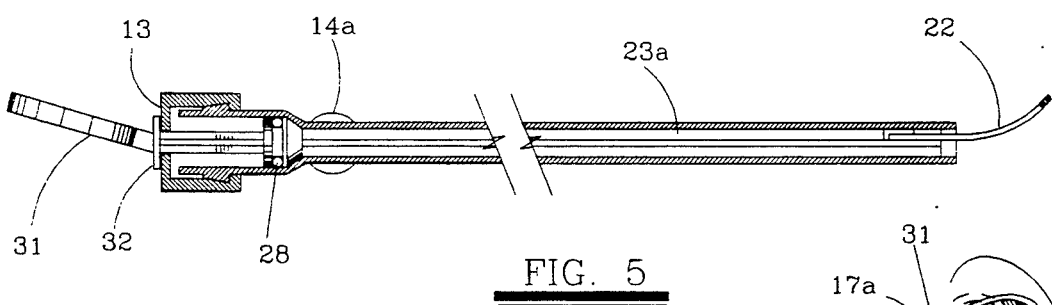
FIG. 5 is a longitudinally extending sectional view through the rake assembly.

Now turning to FIGS. 2, 3 and 4, there is shown the rake assembly of the present invention which includes a solid elongated control mandrel 21 having at one end thereof a stop ring 32 for interface with the cap top 17a when the rake assembly 20 is longitudinally manipulated within the trocar T to the relative telescopically expanded position.

The control mandrel 21 also has defined thereon first and second seal shoulder members 29a, 29b for housing of a circumferentially extending elastomeric o-ring seal element 28 on a seal seat 30 defined around the exterior of the control mandrel 21.

At the end of the control mandrel 21 opposite the handle 31 is flexible means 22 in the form of a metallic u-shaped pin member having tips 27a, 27b. The flexible means 22 is secured on the control mandrel 21 by placing the middle of the "u" configuration of the means 22 through a slot 26. The slot 26 is cut through one of a series of alternating peaks 24 disposed between indentures 25 around the exterior of the control mandrel 21 to provide a cruciform-type configuration 23 around the control mandrel 21. This configuration 23 is provided to enable fluid to pass through the open end 12 and transverse fluid opening 16, and interiorly of the open housing as well as through a cap receiving port 14 on the tubular housing 11. Thus, a series of radially extending fluid passageway members 23a are defined between the peaks 24 and within the indentures 25 on the exterior of the control mandrel 21. This fluid passageway 23a may be utilized to vacuum or drain fluid from the body cavity during surgery, or to introduce a liquid or a gas into the body cavity by use of the trocar T and through the trocar tubular housing 11.

In instances when it is not anticipated that fluid will not be transmitted through the fluid passageway 23a as described above, the port 14 may be sealingly secured by application of the cap 14a thereon. When the cap 14a is removed, a conduit (not shown) is secured at the port 14 on the housing 11 and extends to a vacuum or liquid source (not shown).

OPERATION

When it is desired to use the apparatus of the present invention to hold or move a solid object during surgery, the device, including the tubular housing 11 with the rake assembly 20 disposed therein is introduced through the trocar T. If it is anticipated that fluid will be transmitted through the fluid passageway 23a either into or out of the open end 12 and fluid openings 16, the cap 14a is removed and the appropriate conduit is sealingly engaged on the housing 11 for transmission through the port 14. If not already in the telescopically retracted position, the rake assembly 20 may be placed in such retracted position relative to the tubular housing 11 by holding the device in the hand H and by placing the thumb TH of the operator through the handle 31, or by other manual means, and by pulling on the handle 31 while the trocar T remains stable. Accordingly, the tips 27a, 27b of the flexible means 22 will move towards the shoulder 15 of the tubular housing 11 until such time as the tips 27a, 27b contact the shoulder 15, as shown in FIG. 4, thereby resisting further longitudinal telescopically retracting movement between the tubular housing 11 and the control mandrel 21. In this position, the first seal shoulder 29a will come into contact with the interior of the second opposite end of the tubular housing 11, thereby preventing additional movement of the mandrel 21 relative to the housing 11 in telescopically retracting direction.

Whether or not the control mandrel 21 is in telescopically expanded or retracted position relative to the tubular housing 11, the fluid passageway 23a may be utilized for transmission of fluid either into or out of the body cavity, during the endoscopic surgical operation.

Figure 6:
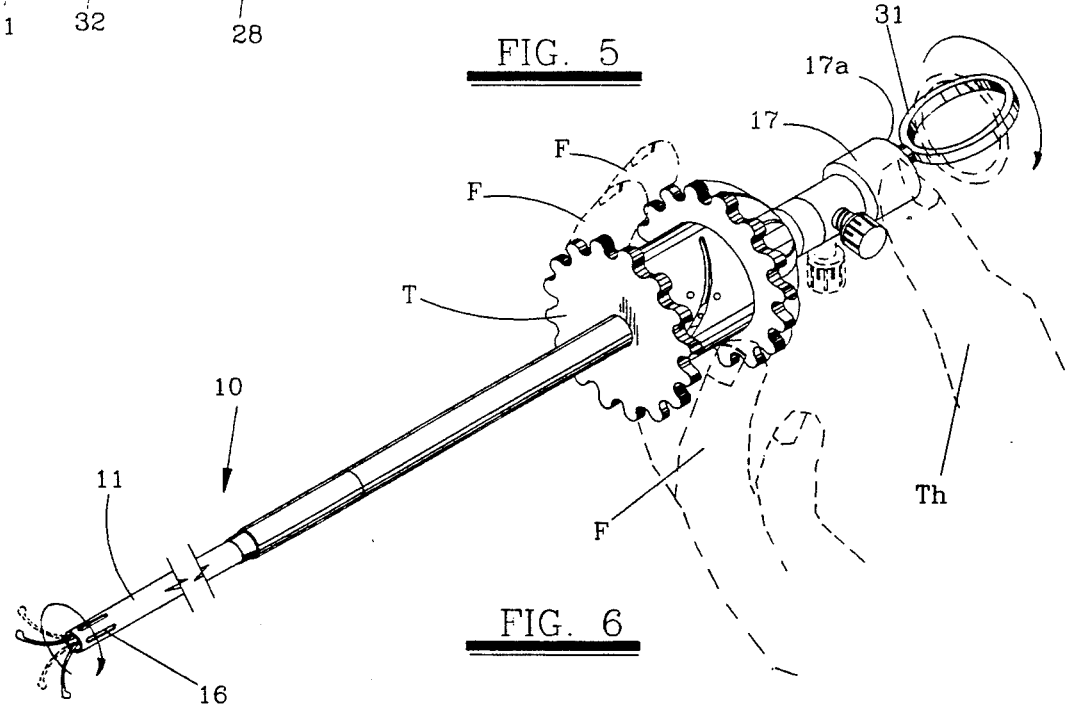
FIG. 6 is an isometric view of the device of the present invention held in the hand of the surgeon, with the rake assembly being rotationally manipulated through the tubular housing, and the tubular housing and rake assembly being in telescopically expanded position relative to one another.

When it is desired to utilize the rake assembly 20 to move, hold or grasp a solid or semi-solid during such surgery, the apparatus is introduced into the trocar T which previously has been placed through the body wall and into the cavity, with the apparatus in the telescopically contracted position (FIG. 4). When activation of the rake assembly 20 is desired, the thumb TH of the operator's hand H is applied on or through the handle 31 while holding the trocar T in place. The control mandrel 21 thus will telescopically expand at the open end 12 relative to the tubular housing 11 to permit the flexible means 21 to extend outwardly of the end 12 and permit the tips 27a, 27b to flex radially outwardly of the shoulder 15 on the housing 11. Thereafter, the control mandrel 21 may be axially rotated relative to the tubular housing 11 either in clockwise or counterclockwise position by rotating the handle 31 (FIG. 6) to cause the flexible means 22 with the tips 27a, 27b to correspondingly rotate to manipulate the solid body to be moved, grasped or held.

Upon completion of the procedure during surgery requiring use of the rake assembly 20, the control mandrel 21 is telescopically contracted relative to the tubular housing 11 by grasping the handle 31 and applying one or more fingers to the cap 17 such that the tubular housing Il is held stable and the control mandrel 21 is longitudinally contractively manipulated relative to the housing 11 until the tips 27a, 27b securely rest on the shoulder 15.

It will be appreciated that the rake assembly 20 may be removed from the tubular housing 11 before, during or after surgery by threadedly disengaging the cap 17 from the housing and withdrawing the control mandrel 21 through the second opposite end 13. During such withdrawal, there may be resistance to continued withdrawal if the tips 27a, 27b come into alignment with the transverse fluid openings 16. However, because of the flexible nature of the pin or means 22, continued pulling, as described, should release the tips 27a, 27b from engagement immediate the opening 16.

Telescopically retracted position between the tubular housing 11 and the control mandrel 21 is detected by the operator by firm resistance to continued telescopically protracting longitudinal movement of the control mandrel 21 by the resisting interface of the tips 27a, 27b on the shoulder 15.

Although the invention has been described in terms of specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed and desired to be secured by Letters Patent is:

1. A combination surgical trocar cannula and rake assembly, comprising: an elongate tubular housing insertable within a trocar and having an open end for introduction through a body wall, and a second opposite end; a control mandrel concentrically disposed within said housing and manipulatable in each of rotational and longitudinal directions relative to said housing; and flexible means for grasping or moving a solid member during surgery, said flexible means being extendable through said trocar housing open end and selectively shiftable in response to relative movement between said tubular housing and said control mandrel between a telescopically retracted radially contracted position and a telescopically extended, radially expanded position immediate said open end, said control mandrel having a cruciform configuration comprising a series of alternating peaks and indentures, said indentures defining said fluid passageway.

2. The apparatus of claim 1 further comprising a fluid passageway intermediate said tubular housing and said control mandrel; and a port disposed through said housing for introduction of a fluid or a vacuum therethrough, said passageway extending from said port through said open end.

3. The apparatus of claim 1 further including: a slot circumscribed on said mandrel for receipt of said flexible means.

4. The apparatus of claim 3, said slot being circumscribed about 180° around the exterior of said control mandrel.

5. The apparatus of claim 1: said housing at said open end providing a circumferentially defined shoulder for receipt of outwardly protruding tip means of said flexible means whereby, upon movement of said mandrel relative to said housing to the telescopically retracted radially contracted position, said tip means and said shoulder are in contact and said tip means are prevented from moving within said housing.

6. The apparatus of claim 1: said housing having at least one transverse fluid opening through said housing and immediate said open end.

7. The apparatus of claim 1 further comprising means to prevent fluid communication between said housing and said mandrel immediate said second end.

8. The apparatus of claim 7 wherein said means to prevent fluid communication comprises an elastomeric o-ring seal element carried on one of said housing and said mandrel for sealing dynamic movements along the other of said housing and said mandrel.

9. The apparatus of claim 7 wherein said o-ring seal is carried on said mandrel, said apparatus further comprising first and second seal shoulders defining a seal seat therebetween for receipt of said o-ring seal.

10. The apparatus of claim 9: a portion of said mandrel extending through said second end, said second end having a shoulder member thereon for interface with one of said seal shoulders to limit relative movement between said housing and said mandrel in one direction.

11. The apparatus of claim 10 wherein, when relative movement between said housing and said mandrel in one direction is limited, said tip means are received on said circumferentially defined shoulder at said open end of said housing.

12. The apparatus of claim 1 further comprising a handle on said mandrel manually controlling relative rotational and longitudinal movements between said housing and said mandrel.

13. The apparatus of claim 1 wherein said flexible means comprises a u-shaped pin member.

14. A endoscopic surgical rake assembly, comprising: an elongate tubular housing insertable within a trocar and having an open end for introduction through a body wall, and a second opposite end; a control mandrel concentrically disposed within said housing and manipulatable in each of rotational and longitudinal directions relative to said housing; and flexible means for grasping or moving a solid member during surgery, said flexible means being extendable through said trocar housing open end and selectively shiftable in response to relative movement between said tubular housing and said control mandrel between a telescopically retracted radially contracted position and a telescopically extended, radially expanded position immediate said open end, said control mandrel having a cruciform configuration comprising a series of alternating peaks and indentures, said indentures defining said fluid passageway.

15. The apparatus of claim 14 further comprising a fluid passageway intermediate said tubular housing and said control mandrel; and a port disposed through said housing for introduction of a fluid or a vacuum therethrough, said passageway extending from said port through said open end.

16. The apparatus of claim 15 further including: a slot circumscribed on said mandrel for receipt of said flexible means.

17. The apparatus of claim 16, said slot being circumscribed about 180° around the exterior of said control mandrel.

18. The apparatus of claim 15: said housing at said open end providing a circumferentially defined shoulder for receipt of outwardly protruding tip means of said flexible means whereby, upon movement of said mandrel relative to said housing to the telescopically retracted radially contracted position, said tip means and said shoulder are in contact and said tip means are prevented from moving within said housing.

19. The apparatus of claim 15: said housing having at least one transverse fluid opening through said housing and immediate said open end.

20. The apparatus of claim 15 further comprising means to prevent fluid communication between said housing and said mandrel immediate said second end.

21. The apparatus of claim 20 wherein said means to prevent fluid communication comprising an elastomeric o-ring seal element carried on one of said housing and said mandrel for sealing dynamic movements along the other of said housing and said mandrel.

22. The apparatus of claim 20 wherein said o-ring seal is carried on said mandrel, said apparatus further comprising first and second seal shoulders defining a seal seat therebetween for receipt of said o-ring seal.

23. The apparatus of claim 22: a portion of said mandrel extending through said second end, said second end having a shoulder member thereon for interface with one of said seal shoulders to limit relative movement between said housing and said mandrel in one direction.

24. The apparatus of claim 23 wherein, when relative movement between said housing and said mandrel in one direction is limited, said tip means are received on said circumferentially defined shoulder at said open end of said housing.

25. The apparatus of claim 15 further comprising a handle on said mandrel manually controlling relative rotational and longitudinal movements between said housing and said mandrel.

26. The apparatus of claim 15 wherein said flexible means comprises a u-shaped pin member.

* * * * *